United States Patent [19]

Chiba et al.

[11] Patent Number: 5,087,817
[45] Date of Patent: Feb. 11, 1992

[54] INFRARED RAY MOISTURE METER

[75] Inventors: Ryuji Chiba; Hitoshi Hara; Tomoyuki Yamada; Kenji Isozaki, all of Tokyo, Japan

[73] Assignee: Yokogawa Electric Corporation, Tokyo, Japan

[21] Appl. No.: 674,810

[22] Filed: Mar. 25, 1991

[30] Foreign Application Priority Data

Apr. 26, 1990 [JP] Japan .................................. 2-111539
Jan. 18, 1991 [JP] Japan ...................................... 3-4544

[51] Int. Cl.⁵ ............................................ G01N 21/35
[52] U.S. Cl. .................................... 250/339; 250/341; 250/359.1
[58] Field of Search ....................... 250/339, 341, 359.1

[56] References Cited

FOREIGN PATENT DOCUMENTS 2044443 10/1980 United Kingdom ................. 250/339

Primary Examiner—Carolyn E. Fields
Attorney, Agent, or Firm—Moonray Kojima

[57] ABSTRACT

The invention relates to an infrared ray moisture meter which measures moisture of paper using absorption of infrared rays, and in which infrared rays being penetrated and scattered by the paper are sufficiently independent of whether the paper is thin or thick, in which sensitivity is high, in which attenuation of rays is small and error due to misalignment in the XY direction is small. Also, concurrently, in the invention, adverse influence due to quality of the paper is reduced by applying infrared rays which are absorbed by moisture, infrared rays which are absorbed by cellulose, and infrared rays which are not absorbed by moisture or cellulose, and by computing the value of moisture from signals detected from the application of the different infrared rays. In one embodiment a device is provided with a shielding plate having two mirrored surfaces disposed between the paper being measured and a lower one of a pair of reflectors.

12 Claims, 13 Drawing Sheets

Fig.10

|  | Sample (5 Specimens) || Newsprint (7 Specimens) ||
|  | Standard Deviation | Maximum Error | Standard Deviation | Maximum Error |
| --- | --- | --- | --- | --- |
| Two-Filter Method | 1.00% | +3.65%<br>-1.13% | 0.37% | +1.35%<br>-0.47% |
| This Invention | 0.62% | +1.82%<br>-1.12% | 0.11% | +0.20%<br>-0.35% |

INFRARED RAY MOISTURE METER

BACKGROUND OF THE INVENTION

1. Field of Invention

This invention relates to an apparatus for measuring moisture, for example, moisture of paper in a paper making machine.

2. Description of the Prior Art

FIGS. 1-3 depict conventional moisture meters for measuring moisture of paper, for example, in a paper making machine. In FIG. 1, a light emitting portion 1 and a light detecting portion 2 are disposed facing each other with paper 3, whose moisture is to be measured, disposed therebetween. At light emitting portion 1, rays from a light source 6 are made to be parallel rays by a lens 7, are further made to be intermittent rays by a chopper wheel 8, and are applied to paper 3 through an irradiation window 4. Chopper wheel 8 is provided with a filter 9 which transmits rays, the wavelength of which is 1.94 μm, and which are absorbed by moisture (designated as M rays) and a filter 10 which transmits rays, the wavelength of which is 1.8 μm, and which are not absorbed by moisture (designated as R rays). According to the rotation of chopper wheel 8, M rays and R rays are alternately applied to paper 3. At light detection portion 2, the rays which penetrate paper 3 are introduced through an incidence window 5, focused by a lens 11, and focused on light detector 12. At light detector 12, the M rays and the R rays are detected in time sequence and supplied to computing unit 13. Then, computing unit 13 computes $V_R/V_M$ and outputs the results.

In the conventional moisture meter of FIG. 2, at light emitting portion 1, rays from light source 6 are made to be parallel by lens 7, are made to be intermittent rays by a chopper wheel 8', and are applied to paper 3 through irradiation window 4. Filters, such as mounted on the meter of FIG. 1, are not mounted on chopper wheel 8', and chopper wheel 8' is used solely for the purpose of eliminating the influence of stray light. White light which is applied from irradiation window 4 is multiply reflected at irregular reflection surfaces 16,17 which are provided on the surface of light emitting portion 1 and on the surface of the light detecting portion 2, respectively. Surfaces 16,17 face each other with paper 3 sandwiched therebetween. Then, white light is introduced in light detecting portion 2 from incidence window 5 which is provided in misalignment with respect to irradiation window 4.

At light detecting portion 2, the introduced light is divided into two by a beam splitter 18. One group of divided light is introduced into light detector 12 through filter 9 which transmits the M rays and through lens 11. The other group of divided light is introduced into light detector 12' through filter 10 which transmits the R rays and through a lens 11'. The R rays which are detected by light detector 12 and the R rays which are detected by light detector 12' are supplied to computing unit 13 at the same time. Then, computing of $V_R/V_M$ is conducted and the results are outputted.

FIG. 3 shows another conventional moisture meter, wherein spherical mirrors 20,21 are disposed with the openings covered by dust-proof glass 22,23 and with paper 3 sandwiched therebetween. In this meter, rays which are supplied by light source 6 and which are made to be intermittent rays by chopper wheel 8 having the two kinds of filters that are discussed above, are applied to paper 3 through an irradiation window 5. Then, the rays which penetrate paper 3 or which are scattered by paper 3 reach light detector 12 after penetrating paper 3 a plurality of times by being reflected at the inner surface of the sphere and by being applied to paper 3. The computing of $V_R/V_M$ is conducted in the same manner as in FIGS. 1 and 2 by a computing unit, not shown, using the detected rays and an electrical signal which is related to the moisture of paper 3 is then outputted.

In the conventional moisture meters referred to hereinabove, M rays and R rays are applied to the paper, and the ratio of the output $V_R$ of the R rays which penetrate the paper to the output $V_M$ of the M rays which penetrate the paper (i.e. $V_R/V_M$) is computed and an electrical signal which is related to the moisture weight of the paper is obtained.

In an on-line measurement, since the relationship between the moisture weight and the output of the moisture meter subtly changes depending on the type of pulp from which the paper is made and on the basis weight of the paper, calibration curves are made using samples which are prepared in advance. Then, the calibration curves are inputted to a computer and the calibration curve having characteristics which are the nearest to the type of pulp and basis weight of the paper to be manufactured is selected, and then the moisture weight of the paper is obtained using that calibration curve.

However, the number of calibration curves which can be inputted to the computer is limited, for example, eight, and all objects to be measured can not be covered In the conventional moisture meter, even with respect to paper made from the same type of pulp, if the basis weight is different, the gap between the different calibration curves is large.

FIG. 4 shows calibration curves which are obtained using three different types of samples in the meter of FIG. 2. In FIG. 4, the vertical line designates the output of the meter which is given by $K \cdot (V_R/V_M)$, wherein K is a constant. The horizontal line designates the moisture weight ($g/m^2$) of the paper $C_1$ is the calibration curve when the basis weight of the paper is small. $C_2$ is the calibration curve when the basis weight of the paper is medium. $C_3$ is the calibration curve when the basis weight of the paper is large.

For example, when the moisture weight is 25 $g/m^2$, the output of the meter according to calibration curve $C_1$ is the smallest and the output of the meter according to calibration curve $C_3$ is the largest. The reason that the output according to calibration curve $C_3$ is larger even when the moisture weight is the same is that, when the basis weight is large, the number of times reflection and scattering occurs within the paper increases, the optical path length becomes substantially longer, the M rays are absorbed by moisture more, and the value of output $V_M$ becomes smaller.

When the moisture weight is 25 $g/m^2$, if the output of the meter according to calibration curve $C_1$ is regarded as the standard, there is a gap $D_1$ between the standard and calibration curve $C_3$ of 12.5 $g/m^2$ when converted into moisture weight. If the gap is large, a gap $d_1$ between an object to be measured, which is shown by a broken line, and the calibration curve $C_2$, which is selected as the calibration curve having the characteristics nearest to that of the object, is large. This causes error of measurement. Furthermore, the output according to a conventional meter is shown as moisture weight, but generally, as a value according to which the quality of paper is to be controlled, moisture percentage is more convenient. Thus, in addition to moisture weight, the basis weight of the paper is obtained, to calculate moisture percentage.

Among the conventional meters discussed above, the FIG. 1 meter is advantageous in that it is simple and attenuation of quantity of rays is small But, since the object to be measured is only one point of the paper, there is a problem in that if the paper is thin, the miosture meter cannot be very sensitive.

In the meter of FIG. 2, since the optical axis of the light emitting portion and the optical axis of the light detecting portion are misaligned, the number of times the rays meet the paper is large. However, the range of the rays which are scattered at the paper is 180° at the widest, and the rays which meet the paper only once are included. Thus, the sensitivity of the meter is not satisfactory. Also, there is a problem in that if the optical axis of the light emitting portion is shifted more from the optical axis of the light detecting portion in order to decrease the influence of rays which penetrate the paper only once, the quantity of rays is decreased.

A conventional meter is designed so that the optical axes of the light emitting portion and the light detecting portion may be shifted from each other by about 60 mm, and the distance between the upper reflector and the lower reflector may be about 6-8 mm.

In the meter of FIG. 3, since rays which do not penetrate and are not scattered by the paper many times (that is the low sensitive rays do not meet sufficiently with the water molecules) are included in the rays to be detected, there is a problem in that the sensitivity of moisture detection is low. Also, the sensitivity is different depending on whether the paper is thin or thick. Accordingly, there is a problem in that the influence of the quality of paper is great.

Moreover, in the above conventional meters, if the axis of the head containing the light emitting portion and the axis of the head containing the light detecting portion are misaligned within a horizontal plane, a large error is caused. Accordingly, there is a problem in that a mechanical or electrical correcting means is necessary for correcting the resulting error.

SUMMARY OF THE INVENTION

An object of the invention is to overcome the aforementioned and other deficiencies and disadvantages of the prior art.

Another object is to provide an infrared ray moisture meter in which transmission and scattering of rays by the paper is done sufficiently independent of whether the paper is thin or thick, in which sensitivity is high, and in which attenuation of rays is small and measurement error with respect to misalignment in a horizontal plane is small.

A further object is to provide an infrared moisture meter in which influence of the quality of paper is reduced, in which the shift of calibration curves is small, and in which moisture percentage is directly obtained.

The foregoing and other objects, features and advantages are attained by the invention which encompasses an infrared ray moisture meter for measuring moisture contained in paper, comprising a light detector which detects rays which come through the paper and which generates a signal for measuring moisture; an upper reflector and a lower reflector having returning portions at their peripheries and which are disposed so as to sandwich the paper therebetween; a shielding plate both sides of which are mirror finished and which is disposed between the paper and the lower reflector; applying means for applying to the paper infrared rays of a first wavelength range which are absorbed by moisture, infrared rays of a second wavelength range which are absorbed by cellulose, and infrared rays of a third wavelength range which are absorbed by neither the moisture nor the cellulose; detecting means for detecting the infrared rays of the first wavelength range, the infrared rays of the second wavelength range, and the infrared rays of the third wavelength range, from rays which penetrate and are scattered by the paper, and for generating output signals which correspond to the intensity of the respective ranges of the infrared rays; and calculating means for calculating according to the output signals from the detecting means measurement of the moisture in the paper.

BRIEF DESCRIPTION OF DRAWINGS

FIG. 10 is a table depicting comparison of calibration curve of the invention, and of the conventional meter.

DETAILED DESCRIPTION OF THE PREFERRED EMBODIMENTS

Figure 5:
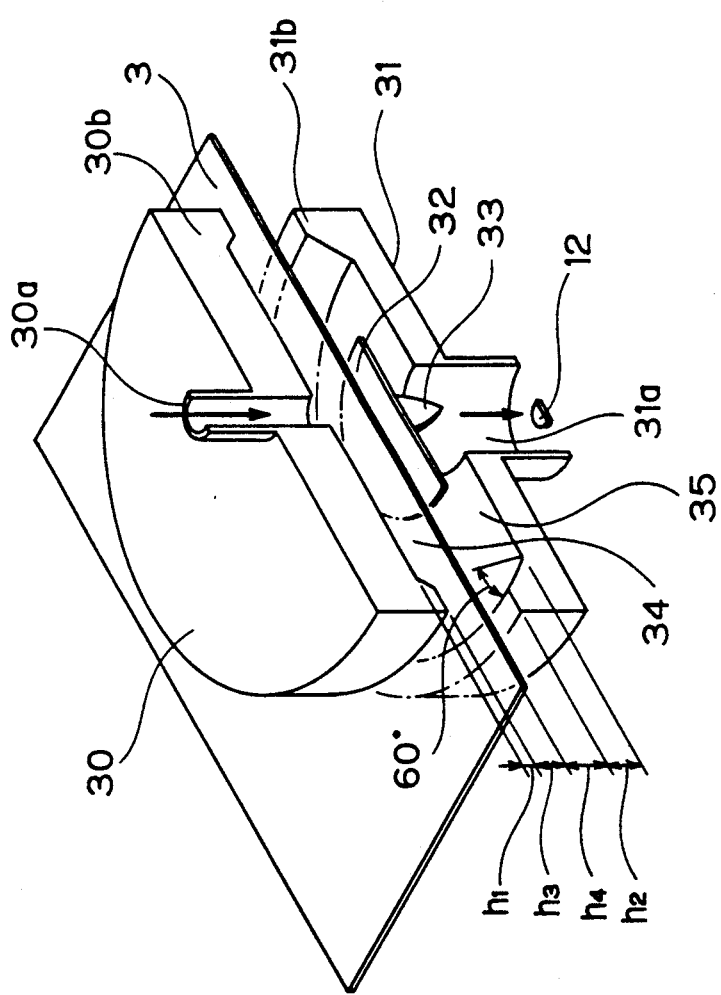
FIG. 5 is a sectional perspective view depicting an illustrative embodiment of the invention.

Turning now to FIG. 5, the upper reflector 30 has a side thereof facing paper 3 which is mirror finished. A light admitting hole 30a is formed at the center of upper reflector 30. A return ring 30b is formed at the peripheral portion of upper reflector 30. Return ring 30b is convex in shape and a section of its inner circumference face meets an angle of about 60° to the perpendicular of the mirror finished face.

Lower reflector 31 also has a side thereof which faces paper 3 which is mirror finished. A light detecting hole 31a is formed at the center of lower reflector 31. A return ring 31b is formed at the peripheral portion of lower reflector 31. Return ring 31b is convex in shape and a section of its inner circumference face meets at an angle of about 60° to the perpendicular of the mirror finished face.

Both of the sides of a shielding plate 32 are mirror finished. A conical protrusion, or conical mirror, 33 has a surface which is mirror finished and is provided at the center of one of the sides of shielding plate 32. Shielding plate 32 is fixed by a plurality of supporting poles, not shown, in the space between lower reflector 31 and paper 3 so as to be as high as the upper portion of return ring 31b of lower reflector 31. Conical mirror 33 is disposed on the side of the light detecting hole 31a. The center of shielding plate 32 is preferably aligned with the axis of upper reflector 30 and the axis of lower reflector 31.

Upper reflector 30 and lower reflector 31 sandwich paper 3 which contains moisture to be measured. Upper and lower reflectors 30,31 are disposed to be as close as possible to each other, taking necessary allowable range into consideration and form with paper 3 light admitting space 34 and light detecting space 35. Although not shown in FIG. 5, a light source is disposed over light admitting hole 30a to supply M rays which have a wavelength of 1.94 μm and are absorbed by moisture, and R rays which have a wavelength of 1.8 μm and are not absorbed by moisture. Various other components, such as calculating unit for calculating moisture based on the output from light detector 12, which necessary components for a moisture meter, are provided at subsequent stages of light detector 12.

In the embodiment, among rays which are applied from the light emitting portion to the surface of paper 3, rays which are scattered at the surface of paper 3 are reflected at upper reflector 30, and rays which penetrate paper 3 are reflected at shielding plate 32 and are returned to paper 3. In this manner, rays which penetrate or are scattered at paper 3 and which are conveyed around, are mainly reflected at the reflecting surface of upper reflector 30, and are returned to the center portion, and then such penetration and scattering at paper 3 are repeated. A part of the rays are reflected between shielding plate 32 and lower reflector 31 and reach conical mirror 33 under shielding plate 32. Conical mirror 33 functions to lead the rays effectively to light detector 12.

One actual embodiment comprised the following dimensions: Outer diameter of upper reflector 30, 60 mm. Outer diameter of lower reflector 31, 60 mm. Height $h_1$ of upper return ring 30b, 2.5 mm. height $h_2$ of lower return ring 31b, 5.0 mm. Distance $h_3$ from upper return ring 30b to the paper 3, 2.0 mm. Distance $h_4$ from lower return ring 31b to paper 3, 2.0 mm. Diameter of shielding plate 32, 30 mm. Distance from surface of shielding plate 32 to paper 3, 2.0 mm. Diameter of light emitting hole 30a, 3 mm. Diameter of light detecting hole 31a, 18 mm. All other conditions were the same as for the conventional meter.

Figure 1:
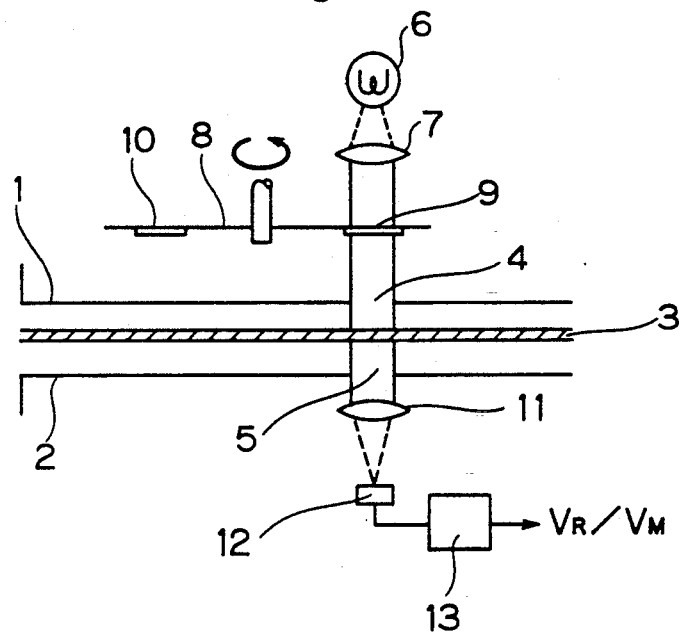
FIGS. 1, 2 and 3 are diagrams depicting conventional moisture meters.
Figure 2:
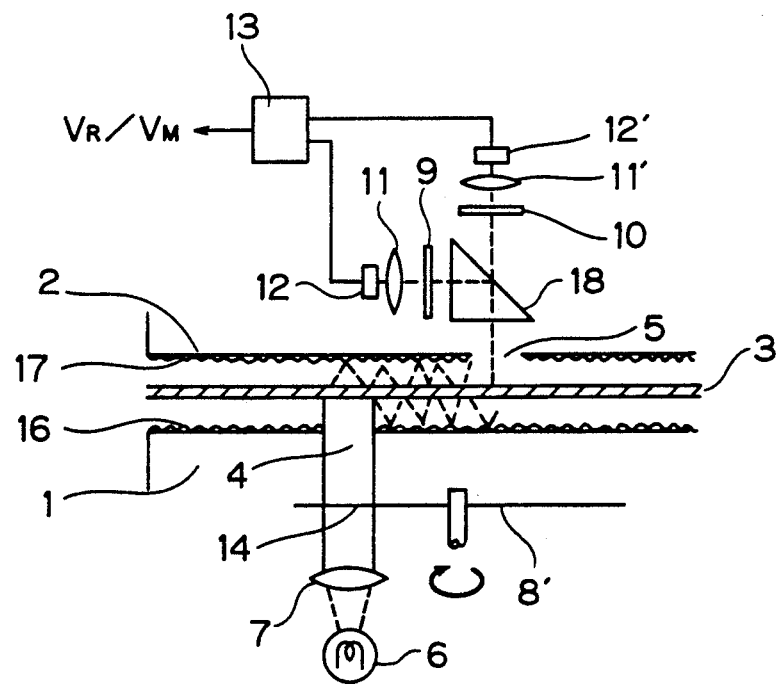
Figure 3:
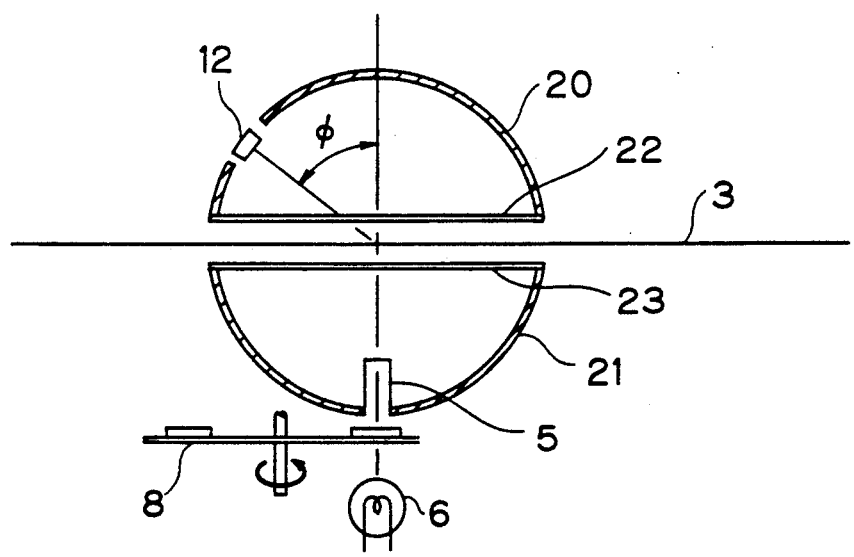
Figure 4:
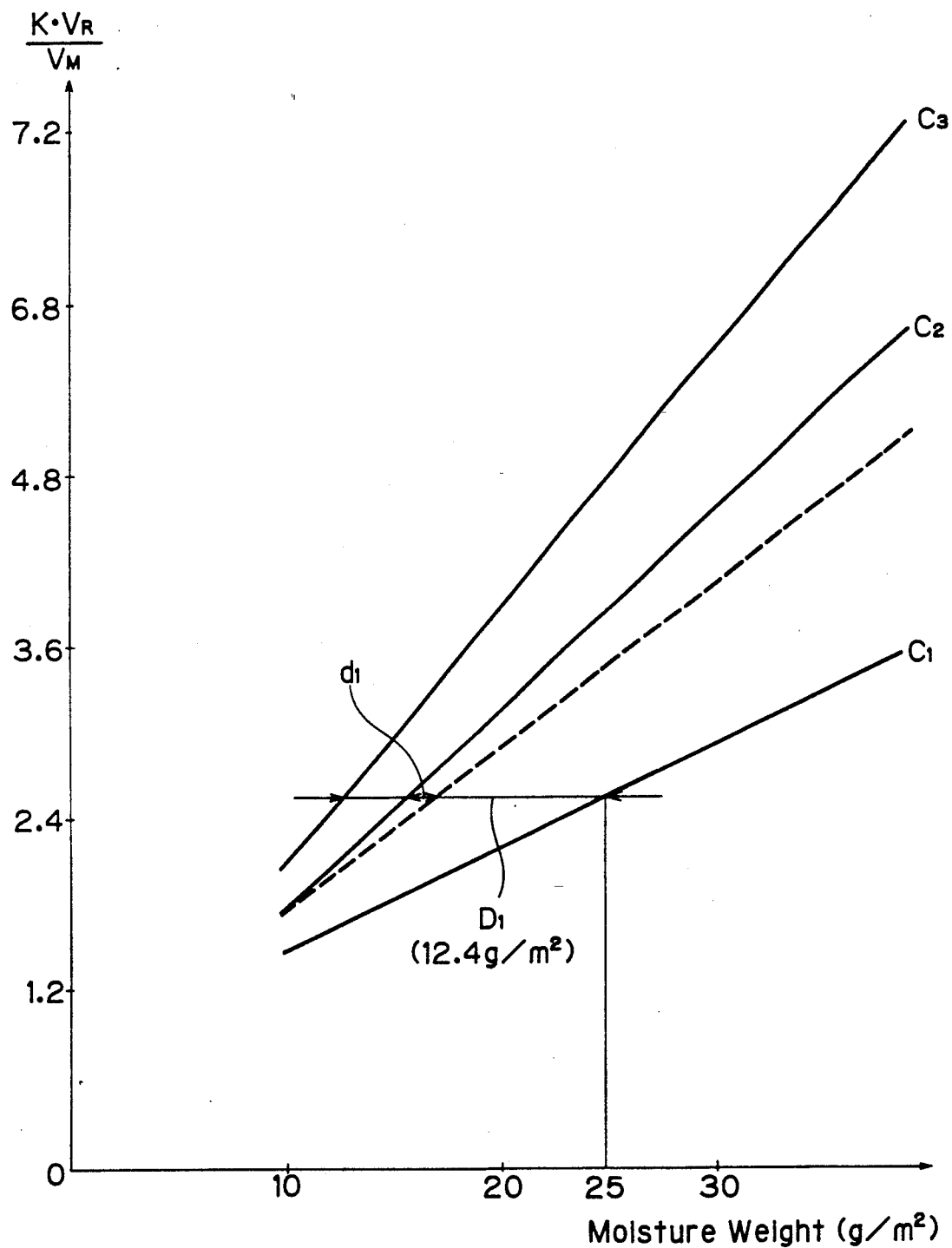
FIG. 4 is a graph depicting calibration curves obtained by the meter of FIG. 2.
Figure 6:
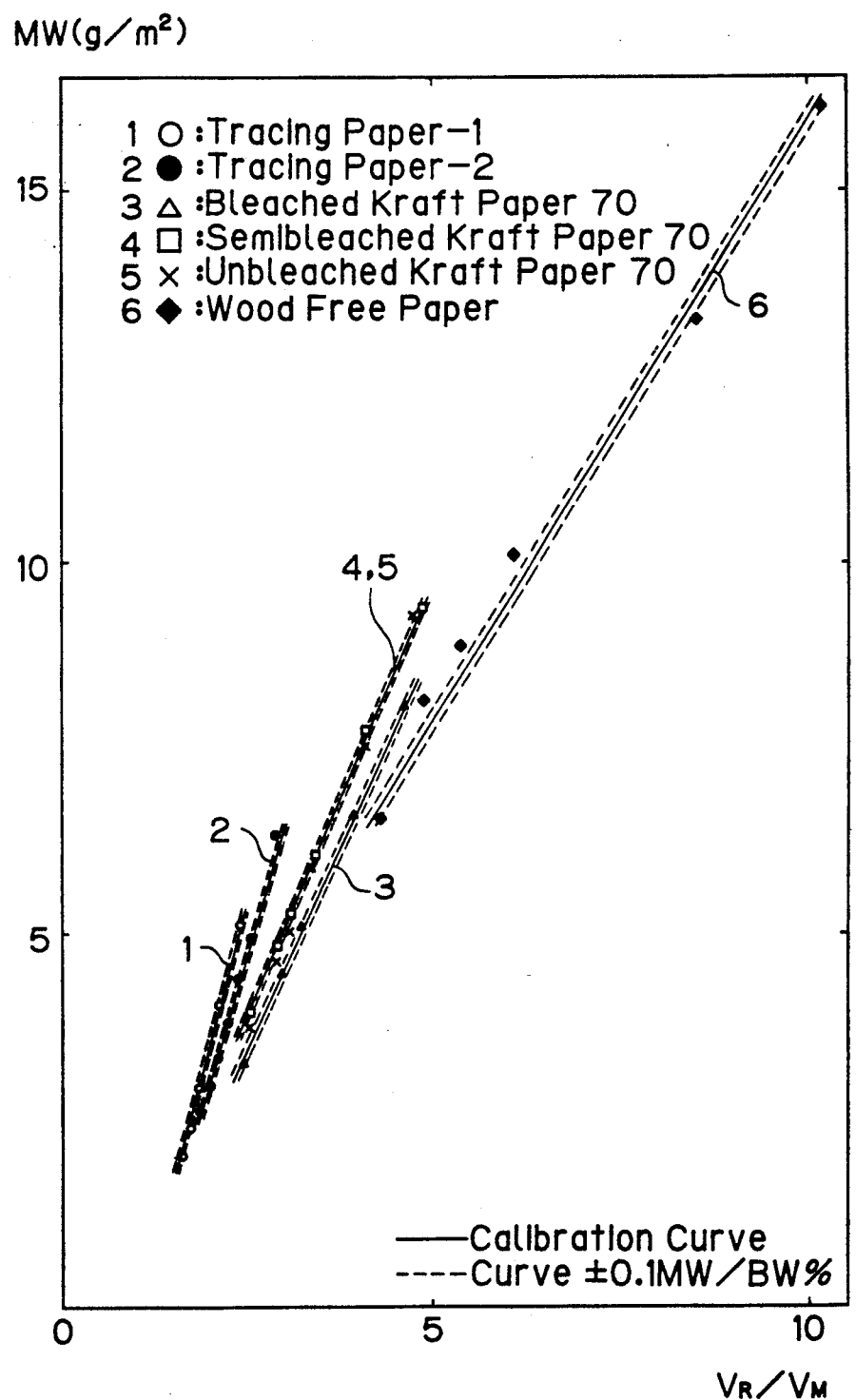
FIG. 6 is a graph depicting the relationship between measurement signal $(V_R/V_M)$, MW, and calibration curves in a conventional moisture meter.
Figure 7:
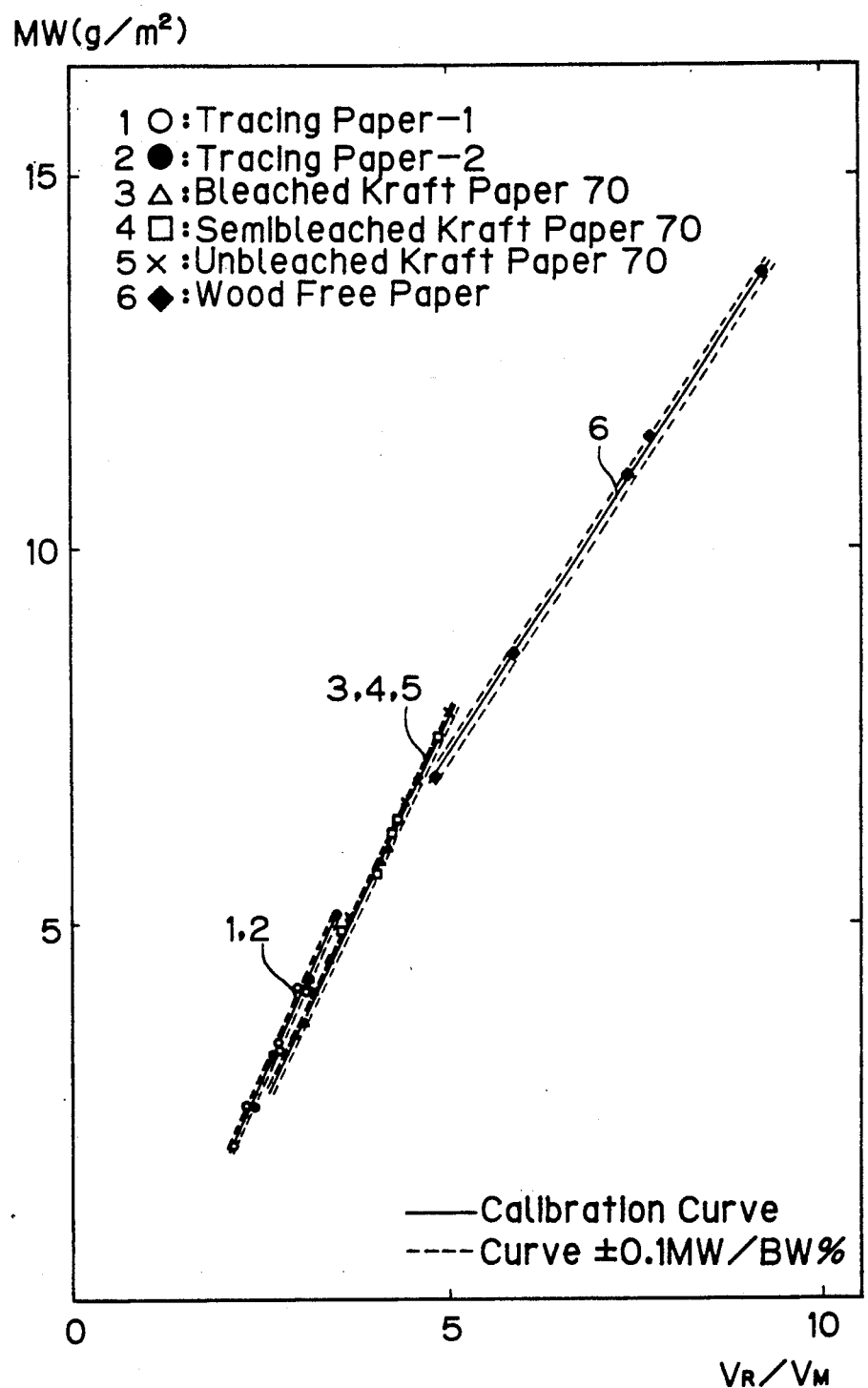
FIG. 7 is a graph depicting the relationship between measurement signal $(V_R/V_M)$, MW, and calibration curves in the invention meter.

FIGS. 6 and 7, respectively, show calibration curves of the conventional meter of FIG. 2, and the moisture meter of the invention, with respect to six types of paper. Moisture weight per unit area MW is found based on measurement signal $V_R/V_M$. Moisture percentage MW/BW×100%, wherein BW is paper weight per unit area, is calculated based on the above value so that measurement is conducted with an accuracy of ±0.1%. Accuracy of ±0.1% means, for example, when the moisture percentage is 5%, the error of measurement is within the range of 4.9% to 5.1%. With the conventional meter, as shown in FIG. 6, five calibration curves are necessary to obtain an accuracy of ±0.1%. On the other hand, with the invention, as shown in FIG. 7, only three calibration curves are needed.

According to the embodiment of FIG. 5, rays which come from the light emitting hole first penetrate or are scattered by the paper 3. These rays are reflected between shielding plate 32 and upper reflector 30 and meet paper 3 a plurality of times. After the rays reach the periphery of shielding plate 32, a part of the rays repeat diffraction between the lower reflector 31 and the rear surface of shielding plate 32 and then reach light detector 12.

On the other hand, rays which repeat the meeting with paper 3 further toward the periphery of the reflectors 30,31 are returned by the return rings 30b,31b, and again reach the periphery of shielding plate 32. A part of the rays are diffracted toward the rear surface of the shielding plate 32, repeat penetration and scattering and reach light detector 12.

As a result, rays which are low in sensitivity for moisture detection, for example, rays which penetrate only once, do not reach the light detector. Thus, sensitivity is improved.

Furthermore, since the moisture meter is arranged to return the rays to the side of the light detector, in the direction of the center, by the return rings, the confining effect is made to be high, the quantity of rays of detection is made to be large, and the same optical system can readily measure moisture of both paper of low basis weight, such as for example about 30 g/m², and paper of high basis weight, such as for example about 150 g/m².

Moreover, since rays which meet with sufficient number of water molecules and which penetrate and are scattered by paper sufficiently are detected independent of whether the paper is thin or thick, the influence of quality of paper on moisture measurement is reduced.

Also, since the rays are returned by the return rings, only a small area of paper to be measured is necessary in order to obtain rays of the same optical path length as that of a conventional meter.

Figure 8:
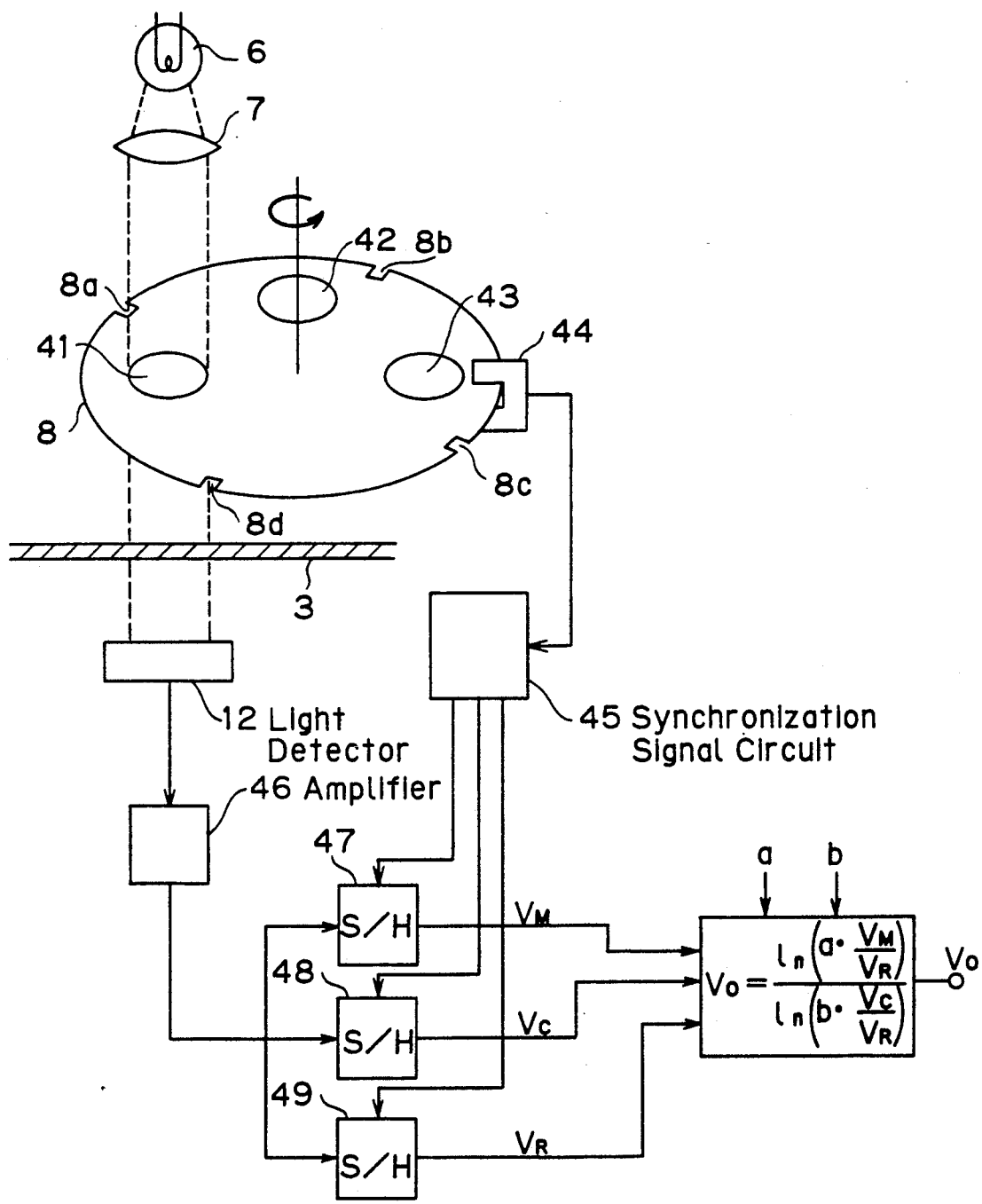
FIG. 8 is a theoretical block diagram depicting the invention using rays of three different wavelength ranges.

FIG. 8 shows an embodiment wherein the influence of quality of paper on moisture measurement is reduced, the shifting of calibration curves is small, and moisture percentage is directly outputted. The embodiment comprises a lamp 6 which supplies rays through condenser lens 7; filters 41,42 each of which selectively transmits infrared rays of a predetermined wavelength range are disposed in concentric circles on a filter wheel 8 which also has four cut-outs 8a,8b,8c and 8c provided on the periphery thereof for generating a synchronization signal; a photo interrupter 44; and a synchronization signal circuit 45 for generating a synchronization signal based on a synchronization pulse from photo interrupter 44. The photo interrupter 44 comprises an LED and a photo transistor disposed so as to face each other and so as to sandwich the peripheral portion of filter wheel 8 so as to generate a synchronization pulse each time cut-out 8a,8b, 8c, and 8d passes the photo interrupter 44.

Paper 3 to be measured for moisture content is disposed between filter wheel 8 and a light detector 13 which applies a signal to amplifier 46. Sample-and-hold circuits 47,48, and 49 convert an AC signal, which is supplied by light detector 12, to a DC signal according to the synchronization signal from synchronization signal circuit 45. An arithmetic circuit 13 calculates signals which are supplied by sample-and-hold circuits 47,48,49 and generates output $V_o$.

The operation of the embodiment is as follows. According to the rotation of filter wheel 8, infrared rays having a wavelength of 1.94 μm, and which pass filter 41, infrared rays having a wavelength of 2.1 μm and which pass filter 42, and infrared rays having a wavelength of 1.8 μm and which pass filter 43, are applied at different times to paper 3. Penetrating rays and scattered rays based on these three types of infrared rays are detected by detector 12. Then, detection output $V_M$ with respect to infrared rays having a wavelength of 1.94 μm, detection output VC with respect to infrared rays having a wavelength of 2.1 μm, and detection output $V_R$ with respect to infrared rays having a wavelength of 1.8 μm, are applied in a form of AC signals to sample-and-hold circuits 47,48,49, respectively. By a synchronization signal, which is supplied to circuits 47,48,49, by synchronization signal circuit 45, the AC signals are converted to DC signals. Then, outputs $V_M$, $V_C$, $V_R$ are outputted from sample-and-hold circuits, respectively, and applied to arithmetic circuit 13.

At arithmetic circuit 13, optimum constants a and b are set and the following calculation is made.

$$V_o = \{ln(a \cdot V_M/V_R)\}/\{ln(b \cdot V_C/V_R)\} \quad (1)$$

As a result, $V_o$ becomes a function of only the moisture weight MW and the cellulose weight CW, namely MW/CW, and one calibration curve is made independent of whether the basis weight is large or small, and what type of pulp is used to make the paper.

In equation (1), error caused by change of optical path length due to enlargement of the basis weight is reduced by dividing $V_M$ by $V_C$, which have the same type of optical path length. The reason for dividing $V_M$ and $V_C$ by $V_R$ is to remove influence of loss due to scattering. Furthermore, since the absorption signal of moisture is divided by the absorption signal of cellulose, a signal is outputted which is related to moisture percentage, i.e. MW/CW, and by conducting ash content correction, moisture percentage alone is outputted.

Figure 9:
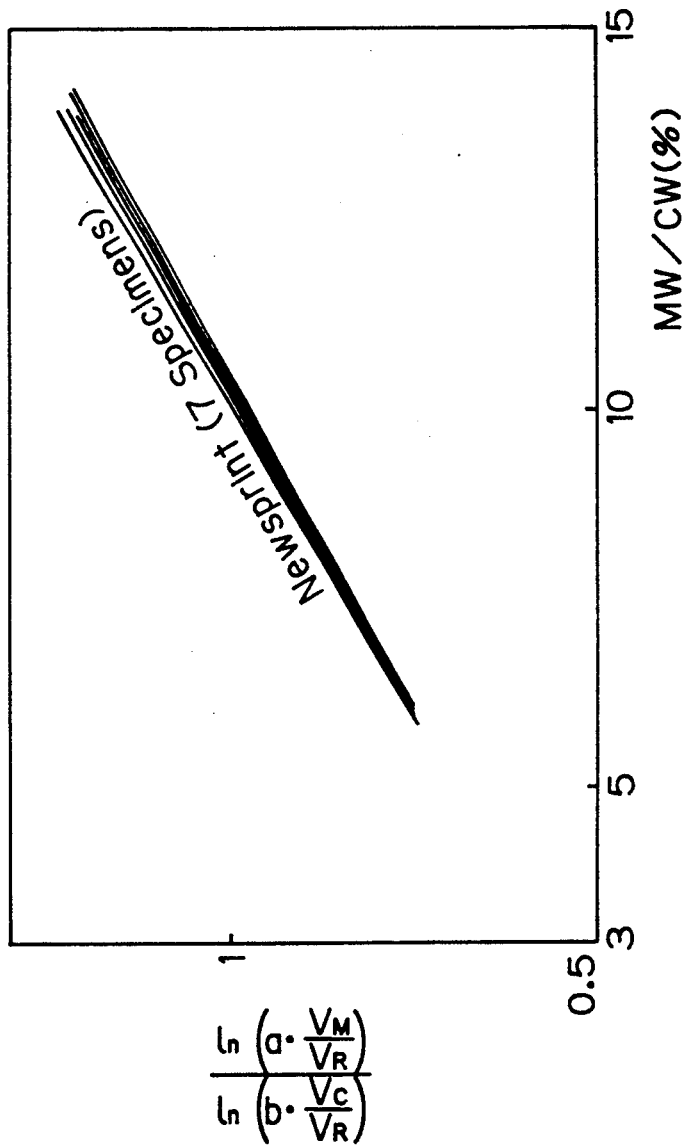
FIG. 9 is a graph depicting calibration curves obtained by the invention.

FIG. 9 shows calibration curves for seven specimen of newsprint using the invention. Only five are separately visible since some of the curves coincide. The vertical line shows $V_o$ referred to hereinabove, and the horizontal line shows MW/CW %.

The moisture percentage is expressed as follows.

$$1/\{1+(CW/MW)\cdot\{1/(1-A)\}\}\cdot 100\% \quad (2)$$

wherein A is ash percentage=ash weight/bone dry weight. Accordingly, if MW/CW is found, moisture percentage alone can be outputted.

In this case, ash content correction has to be conducted with respect to each paper specimen. However, the influence due to change of ash percentage A of equation (2) on moisture percentage is small, and ash percentage, which is found in advance by using samples, can be used.

FIG. 10 shows comparison between the calibration curves of the invention using rays of three different wavelength ranges, and the calibration curves of a conventional meter using a two filter method. As is clear from FIG. 10, with respect to the five samples, the standard deviation of moisture percentage error is reduced from 1.00% to 0.62%. With respect to the seven samples, the standard deviation of moisture percentage error is reduced from 0.37% to 0.11%. With respect to maximum moisture percentage error, for five samples, this is reduced from +3.65,−1.13 to +1.82,−1.12%. With respect to the seven samples, the maximum moisture percentage error is lowered from +1.35, −0.47 to +0.20,−0.35%.

Standard deviation means, the standard deviation of one calibration curve which is obtained from the calibration curves of each sample so that the moisture percentage error may be the minimum (also referred to as a moisture percentage error minimum calibration curve) and the calibration curves of the sample wherein the range of moisture percentage error is from 2% to 12%. The maximum error is the maximum value of plus and minus the moisture percentage error between the moisture percentage error minimum calibration curve and the calibration curves of the sample within the range of 2 to 12%.

In the invention, the infrared rays having a wavelength of 1.94 μm, the infrared rays having a wavelength of 2.1 μm, and the infrared rays having a wavelength of 1.8 μm, are separated by filter wheel and then applied to paper 3. However, white light may be applied to paper 3 and infrared rays of each wavelength may be separated from the light after penetration or after being scattered by paper 3.

Furthermore, in the embodiment, ln is used as the function f, but a function such as log or $X-\{(X-1)^2/2\}-1$ of a polynomial expansion may be used as long as the function of logarithm.

According to the invention, an infrared ray moisture meter has been realized which can measure moisture of paper with reduced influence due to quality of paper, with shift of the calibration curves being small, and which can directly output value of moisture percentage.

Next will be described the invention embodiment wherein error due to misalignment between upper reflector 30 and lower reflector 31, is prevented. Generally, in an on-line measurement of moisture in paper, a light emitting portion and a light detecting portion are disposed on two arms, respectively, which arms are disposed parallel to each other, with the paper moving between the two arms. In order to measure the entire area of the width of the paper, the light emitting portion and the light detecting portion move orthogonally with respect to the machine direction along the arms. Accordingly, the position of upper reflector 30 disposed on the light emitting side and the position of lower reflector 31 disposed on the light detection side (see FIG. 11) are not always aligned with each other and misalignment, for example, in the horizontal direction or the vertical direction is caused. Since this misalignment is followed by measurement error, conventionally, various types of electrical or mechanical correcting means have been proposed. With the embodiment of FIG. 5 the same type of error of misalignment may take place.

When upper reflector 30 and lower reflector 31 are horizontally misaligned, the confining effect of the rays is reduced and the conditions of reflection with shielding plate 32 are changed. Thus, the quantity of rays of detection are decreased and sensitivity might be reduced.

Figure 11:
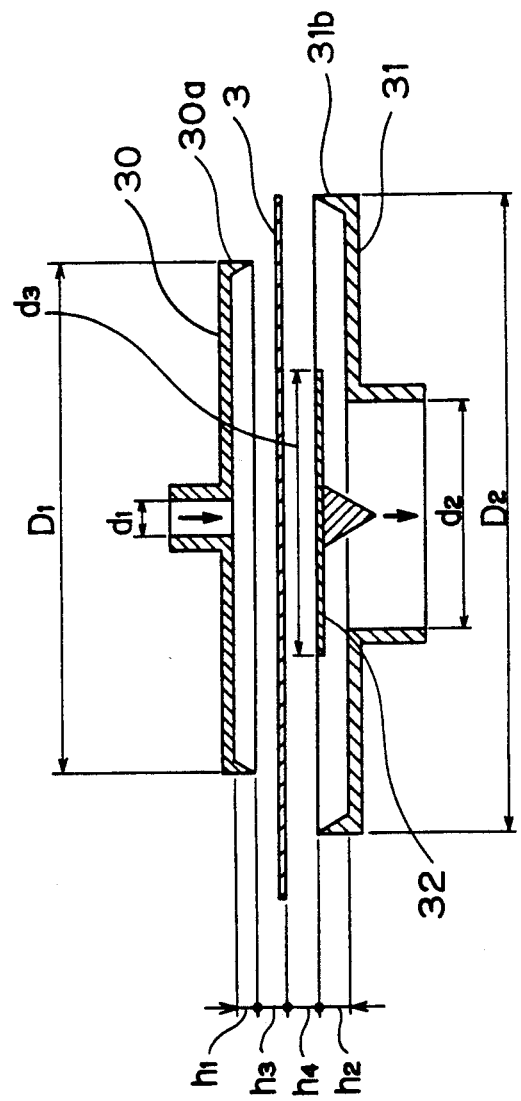
FIG. 11 is a sectional view depicting another illustrative embodiment of the invention, wherein the outer diameter of the upper reflector is smaller than the outer diameter of the lower reflector.

FIG. 11 is a partial sectional view of an embodiment wherein errors otherwise caused by misalignment of the light emitting portion and the light detecting portion, is prevented from occurring. In this embodiment, improvement is made in the horizontal misalignment discussed above. The outer diameter of the upper reflector 30 is made to be smaller than the outer diameter of the lower reflector 31. Lower reflector 31 is necessary for increasing the quantity of the detection rays. On the other hand, since detection of moisture is conducted in the area where the upper surface and the lower surface are overlapped, the range of measuring moisture is the area of the entire upper reflector 30.

According to the embodiment, as far as upper reflector 30 moves horizontally within the area over lower reflector 31, the sensitivity of moisture detection and the quantity of rays are maintained at a predetermined level.

Figure 12:
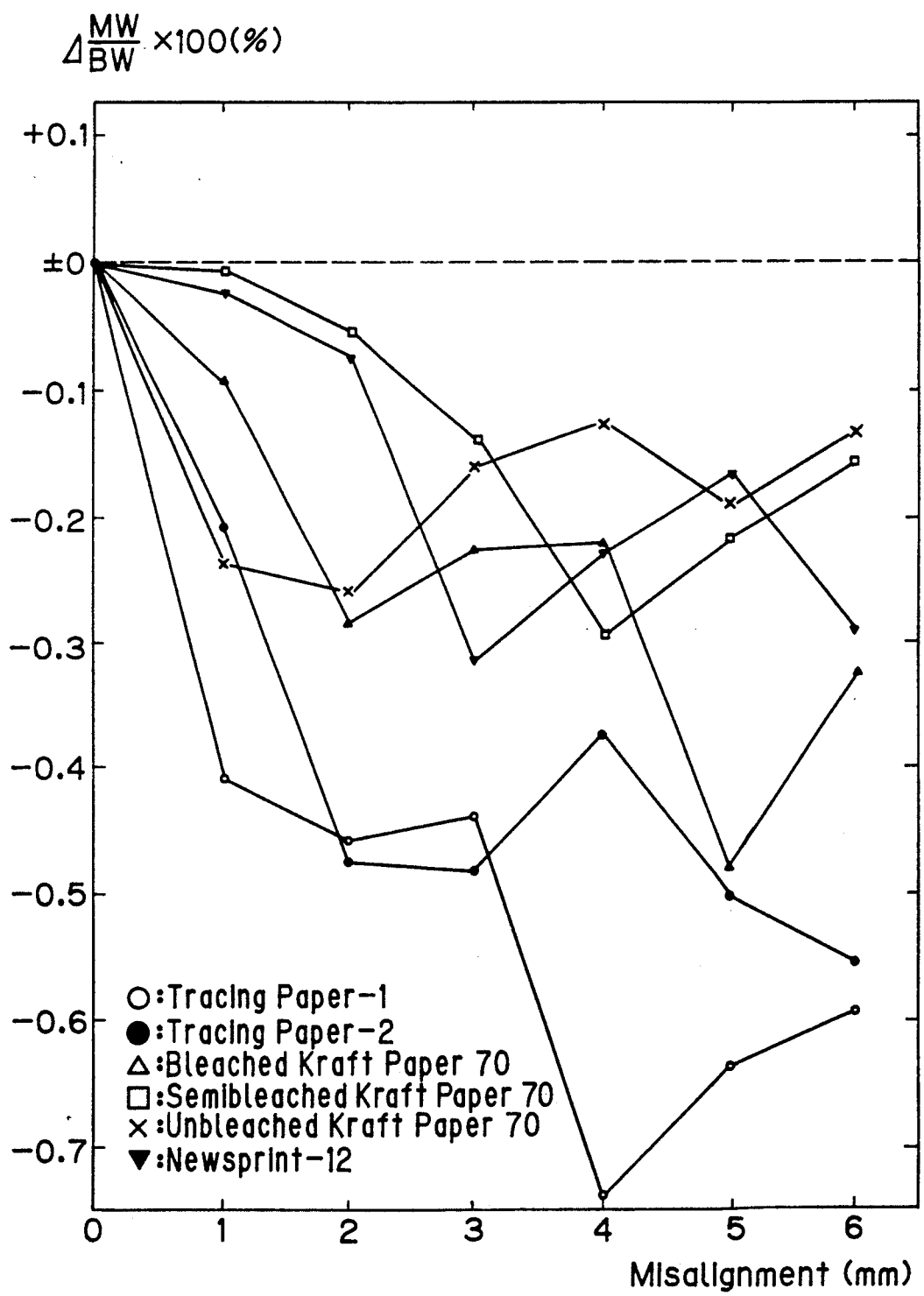
FIG. 12 is a graph depicting the relationship between amount of misalignment and moisture percentage error when the upper and lower reflectors have the same diameters.
Figure 13:
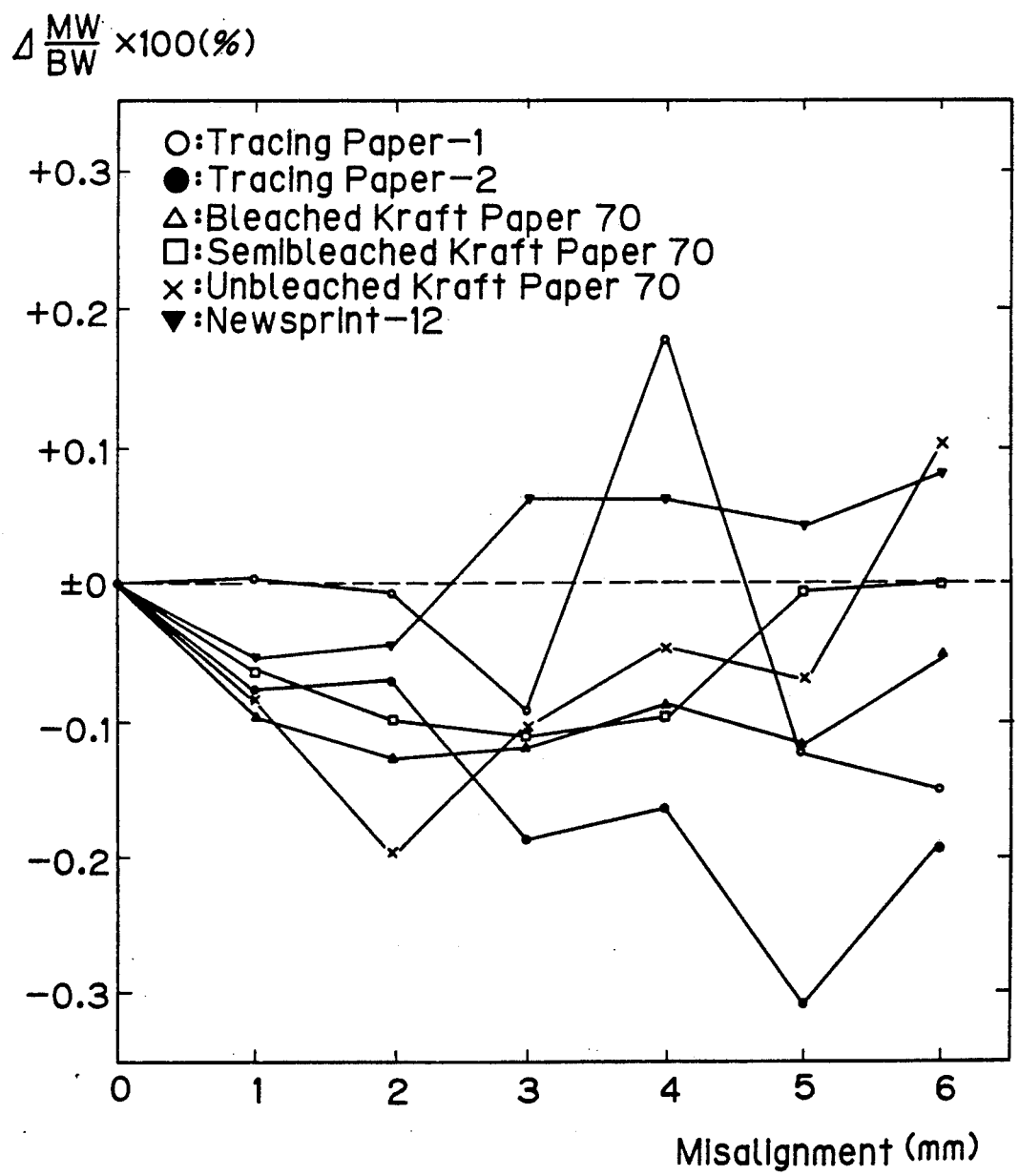
FIG. 13 is a graph depicting the relationship between amount of misalignment and moisture percentage error when the upper reflector has a smaller diameter than the lower reflector.

FIGS. 12 and 13 show an example of an experiment using six different kinds of paper to show the relationship between degree of misalignment and moisture percentage error. FIG. 12 shows the relationship when the outer diameter of the upper reflector 30 is formed to be of the same size as the outer diameter of the lower reflector 31. FIGS. 13 shows the relationship when the outer diameter of the upper reflector is smaller than the outer diameter of the lower reflector 31. In both cases, a moisture meter was used with the rays of three different wavelength ranges as shown in FIG. 8. The results are the errors of moisture percentage as deviated from a standard moisture percentage when there is no alignment, i.e. the upper reflector 30 is coaxial with the lower reflector 31, of moisture percentage $MW/BW \times 100\%$ found by signals which are obtained by moving upper reflector head each 1 mm from the center with the lower reflector head being fixed.

As is clear from FIGS. 12 and 13, by changing the diameter of the upper reflector 30 from that of the diameter of the lower reflector 31, the movement characteristics can be greatly improved. In general the misalignment between the upper and lower reflector heads is about ±1.5 mm. But, in FIG. 12, with respect to the tracing paper −1 and tracing paper −2, the error as to misalignment of 2 mm is over 0.2%. On the other hand, in FIG. 13, when the misalignment is 2 mm, the error is within 0.2% with respect to every kind of paper, and the error of moisture percentage is greatly improved.

In the experiments conducted to obtain data for FIG. 12, a moisture meter was used in which the outer diameters $D_1$ and $D_2$ of the upper reflector and the lower reflector were both 40 mm. For obtaining data for FIG. 13, a moisture meter was used in which the outer diameter $D_1$ of upper reflector 30 was 40 mm and the outer diameter $D_2$ of lower reflector 31 was 50 mm. In both cases, diameter $d_1$ of the light emitting hole, the diameter $d_2$ of the light detecting hole, and the diameter $d_3$ of the shielding plate were 3 mm, 18 mm, and 22 mm, respectively. Height $h_1$ of return ring 30a was 2.5 mm. Height $h_2$ of return ring 30b was 5.0 mm. Distances $h_3$ and $h_4$ from return rings 30a and 30b to paper 3 were both 2.0 mm.

Figure 14:
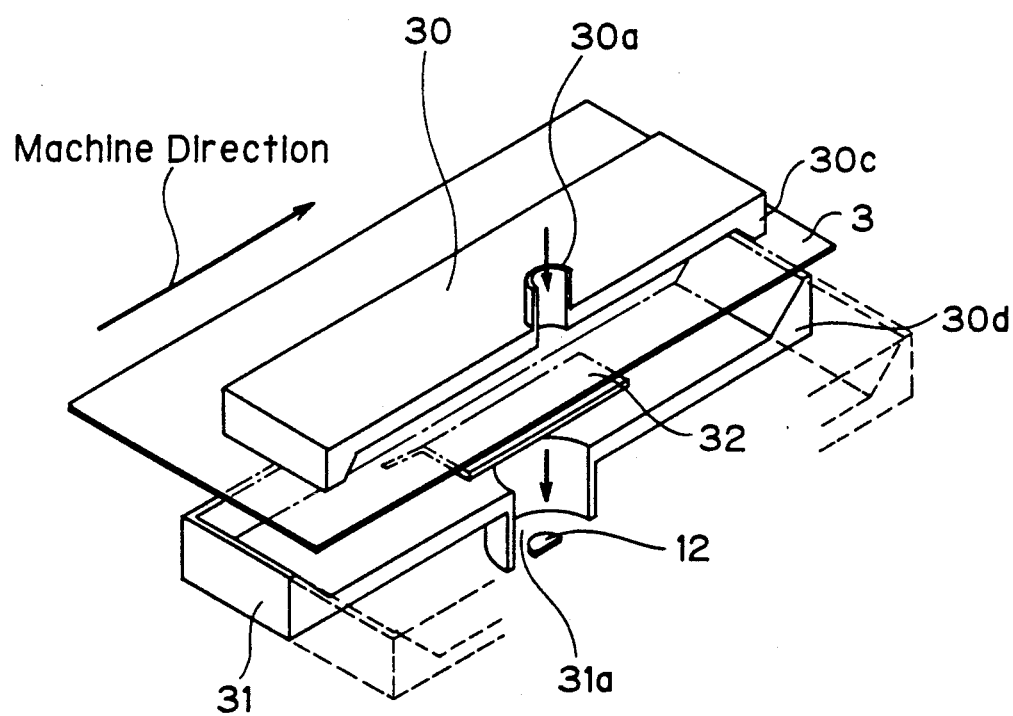
FIG. 14 is a sectional perspective view depicting a further illustrative embodiment of the invention, wherein the measurement width is made to be narrow.

FIG. 14 is a sectional perspective view which shows an embodiment wherein the measurement width is made to be smaller without lowering the sensitivity of detection. Like elements in FIGS. 5 and 14 are designated with the same reference numerals and description thereof is omitted hereat for sake of clarity of description. In the meter of the embodiment, the upper and lower reflectors 30,31 are rectangular in shape. The longer side of upper reflector 30 is 140 mm. The shorter side of upper reflector 30 is 40 mm. The longer side of lower reflector 31 is 150 mm. The shorter side of reflector 31 is 50 mm. Height $h_1$ and height $h_2$ of return rings 30b and 31b are each 9.6 mm from the reflection face. The diameter of light emitting hole 30a is 3 mm and the diameter of light detecting hole 31a is 18 mm. In this embodiment, shielding plate 32 is substantially square with one side being about 40 mm. Both of the sides in the longitudinal direction of the lower reflector 31 are bent so as to be broadened toward the ends with the bent portions being in contact with the lower reflector and being fixed around the center of the lower reflector so that opened portions are located in the machine direction. This embodiment is fixed to a mounting head with its longitudinal direction being along the machine direction.

According to the embodiment, the penetrating and scattered rays do not come from the cross directions and only rays which penetrate and are scattered along the openings in the machine direction are detected. Generally, in an on-line measurement of moisture of paper the measurement width in the cross direction is more important than the measurement width in the machine direction. This arrangement is short in the cross direction and long in the machine direction. Thus, the measurement width can be shortened without lowering the sensitivity of detection In the embodiment, the upper and lower reflectors are rectangular, but, they may be formed to be ellipse-like with the longer dimension being straight and the shorter dimension being semicircular.

The foregoing description is illustrative of the principles of the invention. Numerous extensions and modifications thereof would be apparent to the worker skilled in the art. All such extensions and modifications are to be considered to be within the spirit and modifications are to be considered to be within the spirit and scope of the invention.

What is claimed is:

1. A device for measuring characteristics of paper comprising
an upper reflector which has a return portion at a periphery thereof;
a lower reflector having a return portion at a periphery thereof and disposed opposite said upper reflector with a space therebetween for paper to be measured to be movable therethrough; and
a shielding plate having two mirror finished sides and disposed between said upper reflector and said lower reflector so as to comprise means for reflecting radiation that has passed through paper to be measured.

2. The device of claim 1, wherein the upper reflector and the lower reflector are disc shaped and have substantially the same outer diameters.

3. The device of claim 1, wherein the upper reflector and the lower reflector are disc shaped and have different outer diameters.

4. The device of claim 3, wherein the outer diameter of the upper reflector is smaller than the outer diameter of the lower reflector.

5. The device of claim 1, wherein the upper reflector and the lower reflector are rectangular in shape with the longer dimensions of each being different from each other.

6. The device of claim 1, wherein the upper reflector and the lower reflector are ellipse shaped.

7. An infrared ray moisture meter for measuring moisture contained in paper using absorption of infrared rays, said meter comprising an upper reflector having a return portion at a periphery thereof;

a lower reflector having a return portion at a periphery thereof and disposed opposite said upper reflector with a space therebetween for paper to be measured for moisture content to be movable therethrough;

a shielding plate having two mirror finished sides and disposed between said upper reflector and said lower reflector so as to comprise means for reflecting radiation that has passed through paper to be measured;

means for applying to said paper infrared rays of a first wavelength range which are absorbed by moisture, infrared rays of a second wavelength which are absorbed by cellulose, and infrared rays of a third wavelength range which are absorbed by neither moisture nor cellulose;

detecting means for detecting the infrared rays of said first wavelength range, the infrared rays of said second wavelength range, and the infrared rays of the third wavelength range, and for generating output signals corresponding thereto; and calculating means for calculating the value of moisture of the paper from the output signals from the detecting means.

8. The meter of claim 7, wherein the upper reflector and the lower reflector are disc shaped and have substantially the same outer diameters.

9. The meter of claim 7, wherein the upper reflector and the lower reflector are disc shaped and have different outer diameters.

10. The meter of claim 9, wherein the outer diameter of the upper reflector is smaller than the outer diameter of the lower reflector.

11. The meter of claim 7, wherein the upper reflector and the lower reflector are rectangular in shape with the longer dimensions of each being different from each other.

12. The meter of claim 7, wherein the upper reflector and the lower reflector are ellipse shaped.

* * * * *